(12) United States Patent
Hotier et al.

(10) Patent No.: US 7,582,207 B2
(45) Date of Patent: *Sep. 1, 2009

(54) PROCESS AND DEVICE FOR SIMULATED MOVING BED SEPARATION WITH A REDUCED NUMBER OF LARGE DIAMETER VALVES

(75) Inventors: Gerard Hotier, Rueil Malmaison (FR); Philibert Leflaive, Mions (FR); Sylvain Louret, Lyons (FR); Frederic Augier, Saint Symphorien d'Ozon (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 90 days.

This patent is subject to a terminal disclaimer.

(21) Appl. No.: 11/907,625

(22) Filed: Oct. 15, 2007

(65) Prior Publication Data

US 2008/0121586 A1 May 29, 2008

(30) Foreign Application Priority Data

Oct. 16, 2006 (FR) .................................. 06 09192

(51) Int. Cl.
*B01D 15/08* (2006.01)
(52) U.S. Cl. .................................... 210/198.2; 210/659
(58) Field of Classification Search ................. 210/635, 210/656, 659, 662, 198.2
See application file for complete search history.

(56) References Cited

U.S. PATENT DOCUMENTS

| | | | |
|---|---|---|---|
| 4,434,051 A | | 2/1984 | Golem |
| 5,705,061 A | * | 1/1998 | Moran ...................... 210/198.2 |
| 5,882,523 A | * | 3/1999 | Hotier et al. ................. 210/659 |
| 5,972,224 A | * | 10/1999 | Hotier et al. ................. 210/659 |
| 6,017,448 A | * | 1/2000 | Hotier et al. .............. 210/198.2 |
| 6,093,317 A | * | 7/2000 | Capelle et al. ............ 210/198.2 |
| 6,146,537 A | * | 11/2000 | Ferschneider et al. ....... 210/659 |
| 6,156,197 A | * | 12/2000 | Dessapt et al. ............ 210/198.2 |
| 6,224,762 B1 | * | 5/2001 | Ferschneider et al. ..... 210/198.2 |

(Continued)

FOREIGN PATENT DOCUMENTS

EP 0923970 A1 6/1999

(Continued)

*Primary Examiner*—Ernest G Therkorn
(74) *Attorney, Agent, or Firm*—Millen, White, Zelano & Branigan, P.C.

(57) ABSTRACT

The invention concerns a simulated moving bed (SMB) separation device and process comprising a column, beds $A_i$ of adsorbent separated by plates $P_i$ with a single distribution and extraction network for fluids, in particular feed F, desorbant D, raffinate R and extract E, and a plurality of two-way valves for distribution of said fluids, said valves being limited in number and in particular with dimensions that are smaller than in the prior art. According to the invention, the column is divided into a plurality of sectors $S_k$ with 2 superimposed plates, each sector $S_k$ comprising an external principal bypass line $L_k$ connected to each plate $P_1$ of $S_k$ via a large diameter plate valve $V_1$ and an external secondary bypass line $M_k$ comprising a small diameter valve $V_{Mk}$ connected to the adjacent sector $S_{k-1}$. Each line $L_k$ comprises a flow limitation means, and is connected to each of the fluid networks F, D, R, E via a single large diameter valve for sequential supply or withdrawal of the corresponding fluid F, D, R or E to or from the sector Sk under consideration.

15 Claims, 3 Drawing Sheets

U.S. PATENT DOCUMENTS

Figure 1:
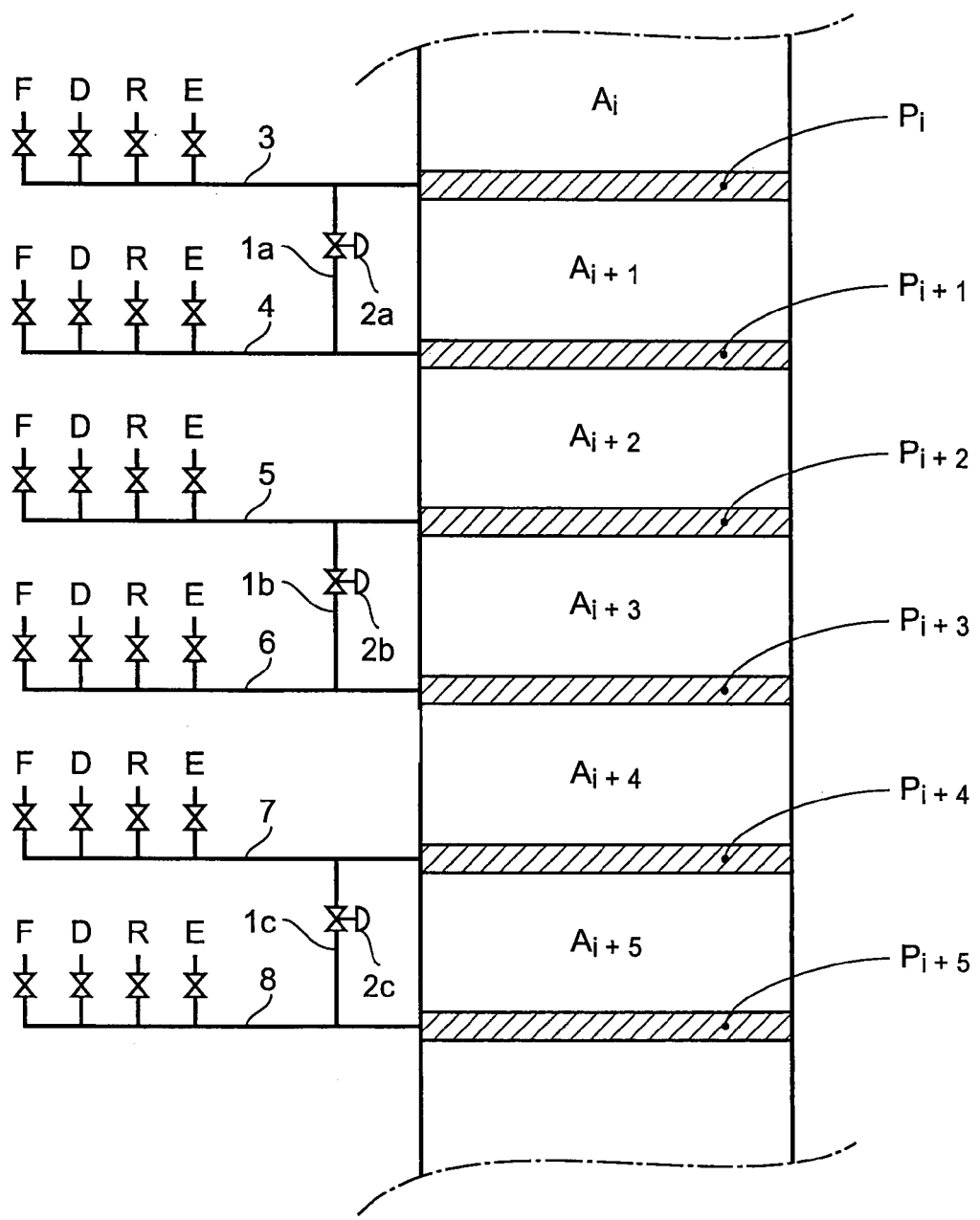

| | | |
|---|---|---|
| 6,402,959 B1 * | 6/2002 | Dessapt et al. .............. 210/656 |
| 6,454,948 B2 * | 9/2002 | Ferschneider et al. ....... 210/659 |
| 6,537,451 B1 * | 3/2003 | Hotier .................... 210/198.2 |
| 6,797,175 B2 * | 9/2004 | Hotier ........................ 210/659 |
| 7,288,200 B1 * | 10/2007 | Hotier et al. ................ 210/659 |
| 2001/0008220 A1 * | 7/2001 | Ferschneider et al. ....... 210/634 |
| 2003/0127394 A1 | 7/2003 | Hotier |
| 2005/0269268 A1 * | 12/2005 | Hotier ....................... 210/659 |
| 2006/0006113 A1 * | 1/2006 | Couenne et al. ............. 210/659 |
| 2008/0041788 A1 * | 2/2008 | Hotier et al. ................ 210/659 |
| 2008/0121586 A1 * | 5/2008 | Hotier et al. ................ 210/659 |
| 2008/0237132 A1 * | 10/2008 | Hotier et al. ................ 210/659 |

FOREIGN PATENT DOCUMENTS

| | | |
|---|---|---|
| EP | 1325772 A | 7/2003 |
| FR | 2782657 A1 | 3/2000 |

* cited by examiner

PROCESS AND DEVICE FOR SIMULATED MOVING BED SEPARATION WITH A REDUCED NUMBER OF LARGE DIAMETER VALVES

FIELD OF THE INVENTION

The invention relates to the field of separation of natural or chemical products which are difficult to separate by distillation. A family of processes and associated devices is used which are known as "chromatographic" or "simulated moving bed" or "simulated counter-current" or "simulated co-current" separation devices which we shall hereinafter term "SMB".

A non-exclusive list of the fields concerned is:
separation of normal paraffins from branched paraffins, naphthenes and aromatics;
olefin/paraffin separation;
separation of para-xylene from other isomers in C8 aromatics;
separation of meta-xylene from other isomers in C8 aromatics;
separation of ethylbenzene from other isomers in C8 aromatics.

In addition to the refinery and petrochemicals plant, there are may other applications, including glucose/fructose separation, the separation of positional isomers of cresol, optical isomers, etc.

PRIOR ART

SMB chromatographic separation is well known in the art. In general, a simulated moving bed comprises at least three chromatographic zones, advantageously four, five or six zones, each of said zones being constituted by at least one bed or a portion of a column and included between two successive supply or withdrawal points. Typically, at least one feed F to be fractionated and a desorbant D (sometimes termed the eluent) are supplied and at least one raffinate R and extract E are withdrawn. Sometimes, an extract-rich reflows RE is also supplied. It is also possible to use not only a raffinate R but two raffinates R1 and R2. thus, there are generally 4, 5 or 6 process fluids which are supplied or withdrawn sequentially. The supply and withdrawal points are modified over time, typically shifted towards the bottom of a bed in the direction of flow in a synchronous manner.

A plurality of advantageous variations can improve the function of that type of unit by making asynchronous permutations. Put simply, such asynchronous permutations act to compensate for the dead volume(s) of the recirculation pump (s), as indicated in U.S. Pat. No. 5,578,215, to work with a constant recycle rate on the recirculation pump to eliminate jerky flow rates and pressure, as indicated in U.S. Pat. No. 5,762,806, or finally to operate with at least two chromatographic zones each one of which is equivalent to a non-integral number of adsorbant beds. This latter variation, as indicated in U.S. Pat. Nos. 6,136,198, 6,375,839, 6,712,973 and 6,413,419 is known as Varicol. Naturally, these three variations may be combined.

It should be noted that a multi-way rotary valve placing the incoming and outgoing fluids in communication with the beds disposed in the adsorption columns only allows a synchronous type permutation. For asynchronous permutations, a plurality of on-off valves is vital. This technical aspect is described below.

The prior art describes in detail various devices and processes which can carry out the separation of feeds in a simulated moving bed. Particular patents which may be cited are U.S. Pat. Nos. 2,985,589, 3,214,247, 3,268,605, 3,592,612, 4,614,204, 4,378,292, 5,200,075 and 5,316,821. These patents also provide details of the function of a SMB.

SMB devices typically comprise at least one column (and frequently two), adsorbant beds $A_i$ disposed in that column, separated by plates $P_i$ with chamber(s) $C_i$ for distribution and/or extraction of fluids into or from the various beds of adsorbant, and controlled means for sequential distribution and extraction of fluids.

Each plate typically comprises a plurality of distributor-mixer-extractors or "DME" supplied via lines or "distribution/extraction manifolds". The plates may be of any type and any geometry, in particular with panels forming adjacent sectors in the column, for example panels with angular sectors such as those shown in FIG. 8 of U.S. Pat. No. 6,537,451, which are of symmetrical manifold supply, or parallel sectors such as cutouts in a circumference, as indicated in published patent application U.S. Ser. No. 03/0,127,394, which are supplied bi-symmetrically. Preferably, the separation column comprises parallel sector type DME plates and bi-symmetrical supplies. Preferably again, the adsorbant is dense packed. This means that a larger quantity of adsorbant can be used in a given column and increases the purity of the desired product and/or the SMB flow rate.

Distribution over each bed requires a flow from the preceding bed (principal circulating fluid along the principal axis of the column) to be collected, the possibility of injecting therein an auxiliary fluid or secondary fluid while mixing the two fluids to the best possible extent, or the possibility of removing part of the collected fluid, extracting it to send it out of the device and also re-distributing a fluid onto the next bed.

To this end, it is possible to use in a plate $P_i$ chambers $C_{i,k}$ for distribution (injection/extraction) which may be separate or be common with the mixing chambers. Plates $P_i$ with one or more chambers are known, either supplied (or exhausted) separately by different fluids at a given time, or supplied (or exhausted) simultaneously and in parallel by the same fluid at a given time. In the first case, the plate is said to have a plurality of distribution networks and in the second case it has a single distribution network. The invention pertains exclusively to a device comprising plates with a single distribution network.

In general, either all of the fluid or principal flow is passed through the column in a manner described in U.S. Pat. No. 2,985,589, or a large part or all of that flow is evacuated as described in the process disclosed in U.S. Pat. No. 5,200,075.

A generic problem with all SMB devices is minimizing the pollution generated by the liquid present in the various zones and volumes of the supply and withdrawal circuits for the fluids and plates during modifications to the supply and withdrawal points during operation of the SMB. When during the operating sequence a line, chamber or supply zone for a plate $P_i$ is no longer flushed by a process fluid, it becomes a dead zone in which the liquid stagnates, and only moves again when another process fluid moves in it. Since in SMB this is a different process fluid, the liquid in the dead zone is necessarily displaced by a liquid with a substantially different composition. Mixing or circulation over a short time interval of fluids with substantially different compositions thus introduces a deviation from the ideal operation, which proscribes discontinuities in composition.

A further problem may reside in any re-circulation between different zones of the same plate, which thus also induces a deviation from ideal operation.

To overcome these problems linked to re-circulation and dead zones, various techniques are already known in the prior art:

a) flushing of the lines and dead zones by a desorbant or relatively pure product has already been proposed. That technique prevents pollution of the desired product during its extraction. However, since the flushing liquid typically has a composition which is very different from the liquid it displaces, this introduces discontinuities in the composition which are prejudicial to ideal operation. This first flushing variation typically carries out "short duration flushes at a high concentration gradient". These flushes are brief to limit composition discontinuity effects.

b) As described in U.S. Pat. No. 5,972,224, another solution consists of passing the majority of the principal flow towards the interior of a column and a minority of that flow towards the exterior, typically 2% to 20% of the flow, via external bypass lines between neighbouring plates. This flush is typically carried out most of the time or continuously, so that the lines and zones are not "dead" but are flushed. Such a system with flushing via bypass lines is shown in FIG. 1 of U.S. Pat. No. 5,972,224 and repeated in a simplified version in FIG. 1 of the present application. Since the bypass lines are designed for a small flow, they may as a result be small in diameter, and comprise a small diameter valve, which reduces the cost of the system.

A first advantage of such a system is that the injection and withdrawal circuits for secondary fluids are flushed with liquid with a composition which is very close to the displaced liquid since firstly, the bypass derives from a neighbouring plate, and secondly, flushing is substantially continuous rather than discontinuous. Further, the flows in the bypasses are preferably determined so that the transit rate in each bypass is substantially the same as the rate of advance of the concentration gradient in the principal flow of the SMB. Hence, the various lines and capacities are flushed with a fluid which has a composition which is substantially identical to that of the liquid which is found therein and the liquid circulating in a bypass is RE-introduced at a point where the composition of the principal flow is substantially identical. This second variation can thus carry out "long duration flushes with a small or zero concentration gradient".

A second advantage of this long duration flush system (outside the injection or withdrawal periods) is that it can remove the effects of possible RE-circulation between zones of the same plate due to small pressure drop differences.

Regarding the function of a SMB, the controlled fluid distribution and extraction means of a SMB are typically one of the following two major types of technique:

either, for each plate, a plurality of on-off controlled valves for supplying or withdrawing fluids, said valves typically being located in the immediate vicinity of the corresponding plate, and in particular comprising, for each plate $P_i$, at least 4 controlled two-way on-off valves to respectively supply fluids F and D and withdraw fluids E and R;

or a multi-way rotary valve for supply or withdrawal of fluids over all of the plates.

The first technique uses two-way valves, which can be mass produced, resulting in increased reliability and a relatively low unit cost. The second technique uses only a single valve, but that single valve is a multi-way valve (more than 2 paths) and necessarily is of special construction, of large dimensions and extremely complex. Further, this second technology excludes the possibility of asynchronous permutations, as in Varicol devices.

The invention concerns SMB using conventional two-way valves, i.e. using the first of the two techniques described above. In particular, it concerns an improved device for simulated moving bed separation comprising a plurality of two-way on-off valves, generally with a slightly reduced number of controlled valves, and in particular with a substantially reduced number of large opening diameter controlled valves. It can be used both for SMB with synchronous permutations and for SMB with asynchronous permutations, for example a Varicol.

BRIEF DESCRIPTION OF THE INVENTION

The invention concerns an improved device for simulated moving bed separation belonging to the major SMB technique using a plurality of controlled two-way (on-off or progressive opening) valves, typically standard valves mass produced at the required high standard (seal/reliability) at low cost.

One of the essential aims of the invention is to reduce the relative disadvantage of this type of SMB, which is to require a large number of controlled large diameter two-way valves, i.e. with an opening diameter compatible with the movement of fluids in the SMB process at their nominal flow rate. Typically, the invention can substantially reduce the number of large opening diameter controlled valves while preserving the advantage of being able to use effective flushing of dead zones of the "long duration with a small or zero concentration gradient" type.

A further aim of the invention is to provide a device which requires a reduced number of two-way large (opening) diameter valves without the open/close frequency of those valves being increased with respect to the prior art; this along with the reduced number of large diameter valves limits the statistical risks of malfunction and thus increases the reliability of the system.

Finally, in a preferred variation of the device, the number of large diameter valves which allow circulation of the principal fluids of the SMB at their nominal flow rate can be further reduced.

The device of the invention may be used in new facilities, but is also compatible with various existing facilities on which it may be installed, by carrying out limited modifications. It is also compatible with various types and geometries of plates $P_i$, for example plates with angular sector panels or with parallel sectors, provided that said plates (or the majority thereof) are of the single distribution network type, for sequential supply or withdrawal of a process fluid of the SMB.

Thus, a means has been discovered which can substantially reduce the number of principal large diameter controlled valves, corresponding to the sequential inlets/outlets for fluids for the SMB process at their nominal flow rate: in the prior art, for each plate there is at least one set of 4 principal network valves for supply/withdrawal of F, D, R, E. This number is further increased if there are more than 4 process fluids, for example if there are two raffinates R1, R2 or if a reflux RE is used which is rich in the desired product, typically extract. Thus, there are as many large diameter controlled valves per plate as there are process fluids for the SMB, i.e. usually between 4 and 6, limits included.

In the prior art, the bypass lines are only small diameter auxiliary lines which has no effect on the nominal supply or withdrawal flow rate of the fluids F, D, R, E, (E1), (E2), (RE)

but use a substantially smaller flow rate, typically less than 20% of the flow rate circulating in the column, often between 2% and 10% of that flow rate. Thus, they typically include a progressive opening controlled valve (to control the flush rate) with a small opening diameter (or equivalent diameter with the same cross sector of passage).

According to the invention, the column or a principal portion of that column (more than 50% of the height of the column at least) is grouped into superimposed sectors $S_k$, each sector $S_k$ comprising two successive beds of adsorbant $A_i$, $A_{i+1}$, and 2 plates $P_i$, $P_{i+1}$ located respectively immediately below these beds, and also comprising a principal bypass line $L_k$. In contrast to the prior art, the fluids of the SMB use the bypass line $L_k$ at their nominal flow (and not by a small flush flow) and a single set of principal network valves (sequential supply or withdrawal) per column sector (for two plates and not per plate as in the prior art) is used, said large diameter valves being connected to the bypass line $L_k$ to allow circulation of these fluids via $L_k$.

In accordance with the invention, "plate valves" are also provided, i.e. a large diameter valve, respectively $V_i$ or $V_{i+1}$, for each of plates $P_i$, $P_{i+1}$ of $S_k$, as well as additional means for limiting the small flows of flushing fluid moving in $L_k$.

In accordance with the invention, a secondary bypass line $M_k$ connecting sector $S_k$ to the immediately lower sector $S_{k+1}$ is provided. This provides an excellent flush of all of the plates of the SMB and tends to improve the purity of the recovered product, typically the extract.

As will be described below, in particular with respect to the description of FIG. 2, which will provide a clearer picture of the invention, the total number of large diameter controlled valves is reduced.

The invention also concerns a SMB separation process using the device described, in particular for separating an aromatic compound, in particular para-xylene or meta-xylene from a feed of aromatic hydrocarbons containing 8 carbon atoms.

The invention also concerns a SMB separation process using the device described, in particular for separating a normal paraffin hydrocarbon or an olefinic hydrocarbon from a cut comprising such a hydrocarbon.

DETAILED DESCRIPTION OF THE INVENTION

Figure 2:
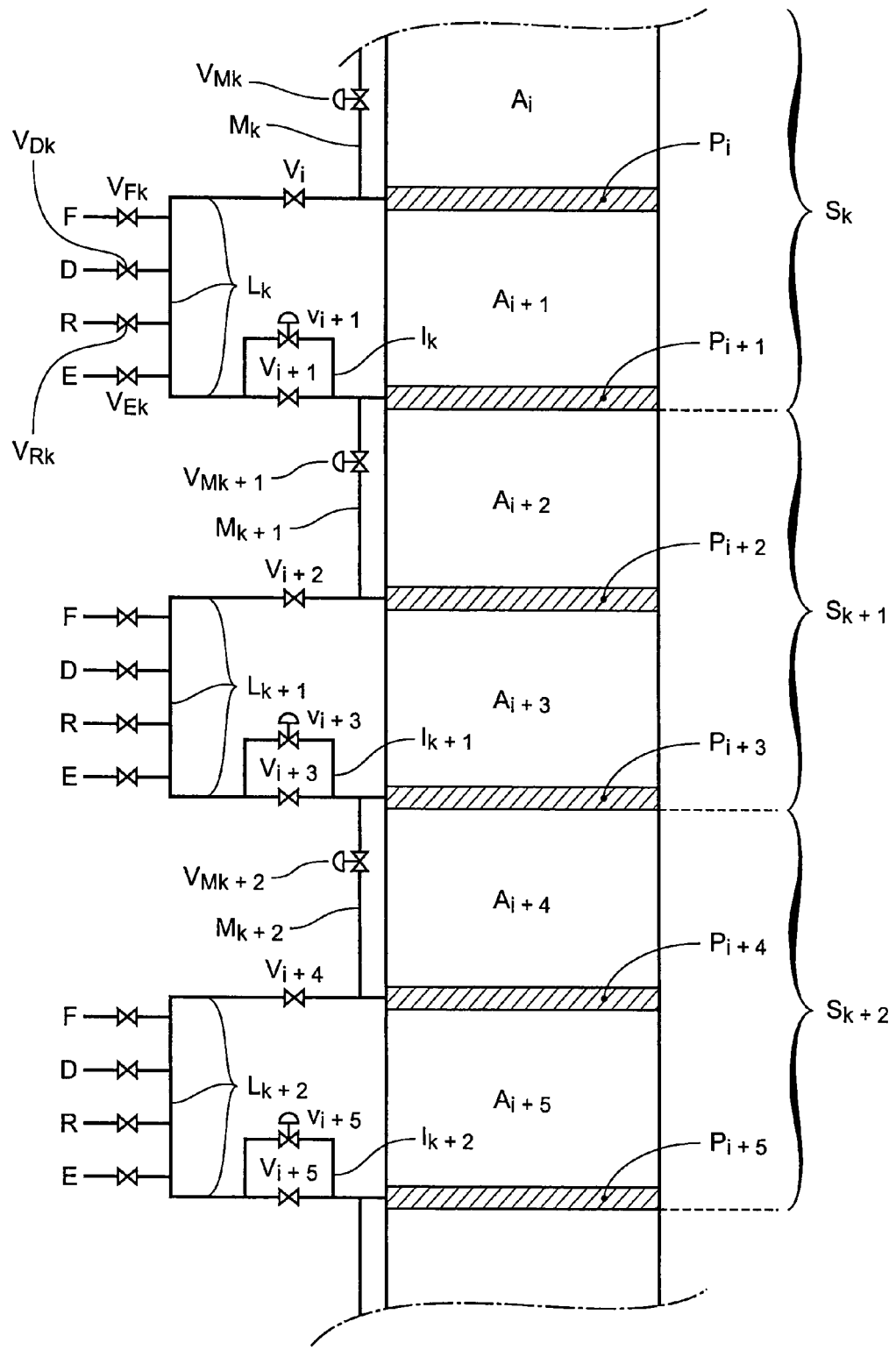
Figure 3:
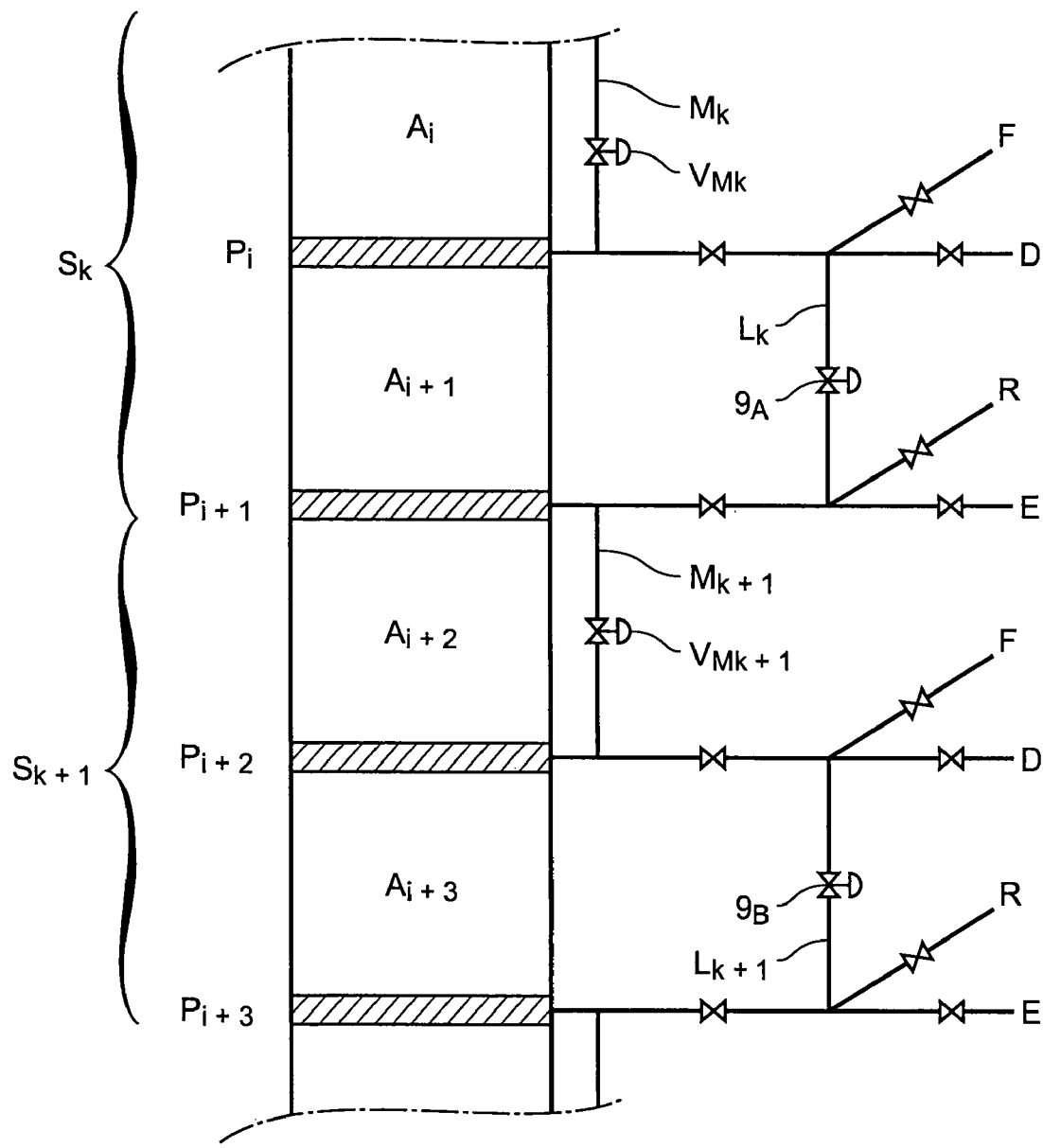

The invention will be better understood from the following description made with reference to FIG. 1 (prior art) and FIGS. 2 and 3 (device of the invention).

To accomplish one of the aims cited above, the invention thus proposes a device which can separate at least one compound from a mixture comprising said compound by simulated moving bed adsorption, comprising:

at least one column comprising a plurality of adsorbant beds $A_i$ separated by distributor/extractor plates $P_i$ for sequential supply and extraction of at least two supply fluids: a feed F and a desorbant D, and at least two withdrawal fluids: a raffinate R and an extract E, $P_i$ being disposed between the bed $A_i$ and the immediately lower bed $A_{i+1}$;

the device also comprising at least one feed network F-Net, a desorbant network D-Net, a raffinate network R-Net and an extract network E-Net, each of said networks being connected to the column via a plurality of lines comprising controlled two-way isolating valves with an opening diameter of $\alpha$ or above, termed network valves, for sequential supply or withdrawal of said supply or withdrawal fluids;

in which the column is divided, over at least the major part of its height, into a plurality of adjacent superimposed sections $S_k$, each sector $S_k$ being essentially constituted by 2 successive adsorbant beds $A_i$, $A_{i+1}$ and by the 2 distributor/extractor plates $P_i$, $P_{i+1}$ which are respectively disposed immediately below $A_i$ and $A_{i+1}$;

each of the distributor/extractor plates $P_i$, $P_{i+1}$ of each of the sectors $S_k$ has a single common network for sequential supply and withdrawal of F, D, R, E;

plates $P_i$, $P_{i+1}$ of each sector $S_k$ are connected together via an external principal bypass line $L_k$ connected to each of plates $P_i$, $P_{i+1}$ of $S_k$ via a connector comprising a single two-way controlled isolating valve which belongs to said plate $P_i$ or $P_{i+1}$, termed a plate valve $V_i$ or $V_{i+1}$, with an opening diameter which is greater than or equal to the value $\alpha$ for sequential supply or withdrawal of said supply or withdrawal fluids in or from $P_i$;

each of said bypass lines $L_k$ comprises at least one controlled means for limiting the flow moving in $L_k$, which is either installed on the line $L_k$ or bypasses a plate valve $V_i$ or $V_{i+1}$ of a plate of $S_k$;

in which the bypass line $L_k$ of each of the sectors $S_k$ is connected to each of the networks F-Net, D-Net, R-Net, E-Net via a single line with an internal diameter of $\alpha$ or more comprising a single network valve, respectively $V_{Fk}$, $V_{Dk}$, $V_{Rk}$, $V_{Ek}$, which has an opening diameter of $\alpha$ or more, for sequential supply or withdrawal of fluid corresponding to F, D, R or E to or from the sector $S_k$ under consideration;

the device also comprising a plurality of external secondary bypass lines $M_k$, each of lines $M_k$ connecting the 2 adjacent sectors $S_{k-1}$ and $S_k$ via 2 connecting points;

the first connecting point being disposed on the connector connecting the lower plate $P_{i-1}$ of the upper sector $S_{k-1}$ between $P_{i-1}$ and the plate valve $V_{i-1}$;

the second connecting point being disposed on the connector connecting the upper plate $P_i$ of the lower sector $S_k$ between $P_i$ and the plate valve $V_i$;

each of the external secondary bypass lines $M_k$ comprising a controlled two-way valve $V_{Mk}$ with an internal opening diameter of $\beta$ or less, in which $\beta \leq 0.6\alpha$.

Typically, $\alpha$ and $\beta$ are selected so as to satisfy the following inequality: 30 mm $\leq 1.7 \times \beta \leq \alpha \leq 600$ mm. It will be seen that valves $V_{Mk}$ with an internal diameter with an opening of $\beta$ or less are much smaller and cheaper than valves with an internal opening diameter of $\alpha$ or more.

In contrast to the prior art device, the device of the invention enables the bypass line $L_k$ to be used to circulate fluids F, D, R, E (and preferably any other process fluids) supplied to the SMB and withdrawn from the SMB at a sector $S_k$, via a single set of corresponding network valves, instead of a set of network valves per plate $P_i$ as in the prior art. This allows a reduction in the overall number of controlled large diameter valves, even when taking into account the addition of supplemental valves, namely plate valves $V_i$, as will be shown below in the description of FIGS. 2 and 3.

The controlled valves—network valves and plate valves $V_i$—are typically high quality valves (reliability, seal, service life) carrying out the sequential operation of the SMB.

More generally, all of the controlled valves ensure the sequential operation of the SMB: network valves, plate valves $V_i$, and also the valves of the controlled means limiting the flow moving in $L_k$ must be considered in the context of the invention as the "principal" valves of the simulated moving bed, connected to the column and controlled by the system controlling the sequential function of the simulated moving bed (computer, programmable automatic machine or other equivalent system).

Certain principal valves of the sequential operation of the SMB have been mentioned above as being unique to the invention: $V_i$ for each plate $P_i$; a single set of network valves $V_{Fk}$, $V_{Dk}$, $V_{Rk}$, $V_{Ek}$, etc for each sector $S_k$. Those valves are exclusively those which allow the sequential operation of the SMB. However, the scope of the invention encompasses using in addition other valves such as occasional secondary isolation valves, typically with a much lower quality, which may or may not be controlled, but which do not participate in the sequential function of the SMB and allow, for example, dismantling of any equipment: pump, or principal valve used for sequential operation, etc.

Typically, in the device of the invention the bypass line $L_k$, which is used to transmit all of the fluids F, D, R, E, etc, at their nominal flow rate, is no longer a small auxiliary line as in the prior art, but generally has an internal diameter which is at least equal to the largest opening diameter of the network valves connected to $L_k$, to be able to circulate fluids F, D, R, E at their nominal flow rate without capacity limitations. The nominal flow rate of a process fluid is by definition the controlled flow rate of this fluid, which is used during the sequential operation of the SMB, for the desired separation.

Because bypass lines $L_k$ are used which can transport relatively high nominal flow rates, controlled means for limiting the flow rate are advantageously used to also carry out bypass circulation in $L_k$ at a low flow rate (typically 2% to 20% of the flow moving in the column). The term "bypass circulation" here means that a (small) fraction of the flow circulating in the column is withdrawn from one plate and re-introduced onto a plate of the same sector $S_k$. The term "control means" typically applies to a controlled valve, typically using a control chain, starting from the information supplied via a flow meter.

To this end, it is possible to use a flow rate regulation valve installed directly on the line $L_k$, as shown in FIG. 3. This valve is thus typically a progressive opening large diameter valve and not a controlled on-off valve (having only 2 possible positions: fully open and closed).

However, in a preferred variation of the invention, shown in FIG. 2, at least one or preferably each of the bypass lines $L_k$ comprises a controlled means for limiting the flow rate in $L_k$ which is not installed directly on $L_k$ but as a bypass around a plate valve of a plate of $S_k$, for example around the valve of plate $V_{i+1}$ of the lower plate $P_{i+1}$. This flow limiter means, disposed on a small auxiliary bypass $l_k$, generally comprises a controlled valve $v_{i+1}$ with a smaller opening diameter than that of $V_{i+1}$, for example with an opening diameter of at most 60%, or 50% that of $V_{i+1}$, for example in the range 10% to 50% of the opening diameter of $V_{i+1}$.

The valve $v_{i+1}$ typically has an opening diameter of $\beta$ or less and often less than or equal to half of $\alpha$. The dimension of this flush rate control valve is advantageously the same as that of the valve $V_{Mk}$ disposed on $M_k$. In both cases, the flush flow rate is regulated. Thus, in the same manner, each of the secondary bypass lines $M_k$ typically comprise at least one controlled flow rate limiting means moving in $M_k$, said means including the valve $V_{Mk}$.

When an internal flush is to be carried out as a bypass via $L_k$ and that internal flow rate (typically moving from the upper plate $P_i$ of $S_k$ towards the lower plate $P_{i+1}$ of $S_k$) is to be limited, the valve of plate $V_{i+1}$ is left closed, the small bypass valve $v_{i+1}$ is opened around $V_{i+1}$, said valve $v_{i+1}$ operating to control the flow rate, and $V_i$ is opened, thus allowing a limited flush deriving from $P_i$ and recycled into $P_{i+1}$ via $L_k$ and $l_k$ to flow (see FIG. 2).

Thus, the use of a small auxiliary bypass $l_k$ allows the use of a valve with a smaller diameter opening than if the flow limiting means were installed on the principal bypass line $L_k$ which is of relatively larger diameter because $L_k$ has to allow the circulation of fluids F, D, R, E etc at their nominal flow rate.

According to the invention, the connector comprising $V_{i+1}$ must be interpreted as not including the small secondary bypass $l_k$ around $V_{i+1}$, nor the small valve $v_{i+1}$ disposed on $l_k$. This connector thus comprises a single valve $V_{i+1}$ to circulate the principal fluids F, D, R, E etc.

Typically, the bypass line $L_k$ has an internal diameter at least equal to the largest opening diameter of the network valves connected to $L_k$. Thus, the diameter of $L_k$ does not constitute a limit to the flow compared with the diameter of the openings in the network valves connected directly to $L_k$.

Preferably, the entire column (with the exception of the head plate, by definition excluded from the term "sector") is constituted by the adjacent superimposed sections $S_k$. In this case, in accordance with the invention the lower outlet line at the column bottom is associated with a plate Pn corresponding to the lower adsorbant bed An. Typically, there is no plate Pn below the adsorbant bed An disposed at the column bottom as there is no need to distribute fluids into a bed immediately below. Further, in accordance with the invention, in this case it is considered that the missing plate Pn is replaced by a lower outlet line of the column, typically connected either to the inlet to the same column via a recirculation pump or to the head of a second separation column.

As mentioned above, the SMB may operate with a reflux RE, comprising extract, or typically rich in the desired product obtained by distilling the extract to eliminate the desorbant (comprising more than 50%, or even 90% or 99% of the desired product). Preferably, the device of the invention then comprises a sequential supply network RE-Net of the reflux RE, said network being connected to each of the sectors $S_k$ via a single line with an internal diameter which is greater than or equal to $\alpha$. Thus, the network of the reflux is connected in identical manner to those of the other process fluids F, D, R, E.

In analogous manner, the SMB may also function with sequential withdrawal of a second raffinate R2, and in this case, the device of the invention preferably comprises a network R2-Net each connected to sectors $S_k$ via a single line with an internal diameter of $\alpha$ or more comprising a single network valve $V_{REk}$, which has an opening diameter of $\alpha$ or more. Thus, the network of the second raffinate is connected in identical manner to those of the other process fluids F, D, R, E (RE).

The invention also concerns a process for separating a product using a device as described above. Typically, during a cycle:
  each line $L_k$ is used sequentially to circulate F, D, R, E and optionally a reflux RE and/or a second raffinate R2 at their nominal flow rate to or from each plate of $S_k$ via the corresponding plate valve and the corresponding network valve in series;
  a flush is carried out at a flow rate which is lower than that of the nominal flow rates of fluids F, D, R, E and optionally RE and/or R2, of each of the principal external bypass lines $L_k$ during at least part of the time in which no network valve connected to $L_k$ is open, using an internal stream deriving from a plate of the device and recycled to another plate of the device, and all internal flushing of $L_k$ is stopped when a network valve connected to $L_k$ is open;
  a flush is carried out at a flow rate which is lower than that of the nominal flow rates of fluids F, D, R, E of each of the external secondary bypass lines $M_k$ for at least part of the time, using an internal stream deriving from a plate of the device and recycled to another plate of the device.

The process of the invention thus uses the SMB device by efficiently carrying out flushes by circulation from plate to plate via external bypass lines $L_k$ and $M_k$. Typically, $L_k$ is flushed by circulating a stream from the upper plate $P_i$ of $S_k$, recycled to the lower plate $P_{i+1}$ of $S_k$.

Typically again, $M_k$ is flushed by circulating a stream derived from the lower plate $P_{i-1}$ of $S_{k-1}$, recycled to the upper plate $P_i$ of $S_k$.

In general, an internal flush of $L_k$ is carried out from an upper plate $P_i$ of $S_k$ to a lower plate $P_{i+1}$ of $S_k$, in any period when $S_k$ is not connected to one of said network fluids sequential supply or sequential withdrawal and which is immediately prior to a period in which one of the network valves connected to $S_k$ is open to supply or withdraw one of said fluids to or from the upper plate $P_i$. This internal flush results in opening $V_i$ in the period preceding a period for supply to or withdrawal from the plate $P_i$ (which also requires opening $V_i$) and avoids opening or closing of $V_i$ between these consecutive periods. The reduction in the number of movements of valves reduces wear on those valves and increases the reliability of the device and the associated process.

Internal flushes of at least two and typically all of the bypass lines $L_k$ is carried out. In general, for a given line $L_k$ (or $M_k$), the internal flush lasts at least 20%, often at least 40% or even at least 50% of the time.

Preferably, for each of the bypass lines $L_k$, $L_k$ is flushed during the whole period of time in which no network valve connected to $L_k$ is open.

Typically, $L_k$ is used by each of fluids F, D, R, E over the whole of its length during a cycle. This prevents the appearance of any dead zones in $L_k$.

The plate valves $V_{i+1}$ and $V_i$ of the connectors connected via an external secondary bypass line $M_k$ are preferably closed when $M_k$ is flushed. This avoids partial mixing of the flush flow with the fluid present in $L_k$.

$M_k$ may be flushed during the whole period in which the plate valves $V_{i-1}$ and $V_i$ of the connectors connected via the secondary external bypass line $M_k$ are closed.

In a variation of the process of the invention, asynchronous permutations of the supply and withdrawal points for fluids F, D, R, E in the column are carried out.

It is also possible to use the device with chromatographic zones at least some of which are equivalent to a non integral number of adsorbant beds, typically a Varicol.

The invention is not limited to a particular separation but may be used for any simulated moving bed separation. As an example, it is possible to carry out a process for separating an aromatic hydrocarbon, for example para-xylene or meta-xylene, from an aromatic feed essentially containing 8 carbon atoms and comprising that hydrocarbon.

It is also possible to carry out a process for separating at least one normal-paraffin hydrocarbon from a feed of hydrocarbons comprising said hydrocarbon or a process for separating at least one olefinic hydrocarbon from a feed of hydrocarbons comprising such a hydrocarbon.

DESCRIPTION OF FIGURES AND OPERATION
OF DEVICES SHOWN

The invention will be readily understood from the accompanying drawings and description in which:

FIG. 1 is a diagrammatic representation of part of a prior art SMB device, with the corresponding network valves;

FIG. 2 diagrammatically shows part of a SMB device of the invention, comprising three superimposed sections $S_k$, $S_{k+1}$, $S_{k+2}$ with the corresponding principal bypasses, secondary bypasses, network valves, plate valves and flow rate limiting valves;

FIG. 3 diagrammatically shows part of a SMB device of the invention, comprising flow rate limiting valves located on lines $L_k$, $L_{k+1}$.

We refer now to FIG. 1, representing part of a chromatographic column of a prior art SMB. Each of the beds of adsorbant, $A_i$, $A_{i+1}$, $A_{i+2}$, $A_{i+3}$, $A_{i+4}$, $A_{i+5}$ is disposed above a plate $P_i$, $P_{i+1}$, $P_{i+2}$, $P_{i+3}$, $P_{i+4}$, $P_{i+5}$ and each of said plates is connected via a line, respectively 3, 4, 5, 6, 7, 8, to each of 4 fluid networks F, D, R, E via a valve (no reference). There are thus 4 principal valves per plate. Further, the plates are connected in pairs via a bypass line $1a$, $1b$, $1c$, typically with a relatively small diameter and comprising a valve with a relatively small diameter ($\beta$ or less), respectively $2a$, $2b$, $2c$, to allow the passage of a limited bypass flow: 2% to 20% of the flow circulating in the column.

In total, then, for each plate Pi, there are 4 principal valves with a relatively large opening diameter of a value of $\alpha$ or more $>\beta$ (compatible with the nominal flow rates of F, D, R, E) and on average 0.5 small diameter valves (one for 2 plates) giving an average of 4.5 valves per plate, including four with a large opening diameter of a or more.

The function of a SMB using such a column is well known to the skilled person. Typically, valve $2a$, $2b$ or $2c$ of a bypass line is open and regulates a limited flush flow when no fluid F, D, R, E is supplied to or withdrawn from one of the 2 plates connected via the bypass line (bypass temporarily in service). In contrast, valve $2a$, or $2b$, or $2c$ of a bypass line is closed when one of fluids F, D, R, E is supplied to or withdrawn from one of the 2 plates connected via the bypass line (bypass temporarily out of service).

FIG. 2 shows part of a column of a device of the invention comprising 3 sectors $S_k$, $S_{k+1}$, $S_{k+2}$, each comprising 2 beds of adsorbant and 2 plates located immediately below. The 2 plates of each sector are connected via a principal bypass line, with a relatively large diameter, typically $\alpha$ or larger, respectively $L_k$, $L_{k+1}$, $L_{k+2}$, which is suitable for circulation of fluids F, D, R, E etc at their nominal flow rate. Each bypass line is connected to a set of 4 network valves with a relatively large opening diameter of $\alpha$ or more for sequential supply and withdrawal of process fluids. In contrast to the prior art, this set of 4 valves supplies not 1 but 2 plates.

Thus, for the first sector $S_k$, there are 4 network valves $V_{Fk}$, $V_{Dk}$, $V_{Rk}$, $V_{Ek}$ supplying both $P_i$ and $P_{i+1}$.

Each plate is also connected to a corresponding bypass line $L_k$ or $L_{k+1}$ or $L_{k+2}$ via a connector (corresponding to the horizontal part of the line in the figure) comprising a single two-way controlled isolation valve belonging to the plate, termed a plate valve: $V_i$, $V_{i+1}$, $V_{i+2}$, $V_{i+3}$, $V_{i+4}$, $V_{i+5}$. Each lower plate valve of a sector: $V_{i+1}$, $V_{i+3}$, $V_{i+5}$ also has a small secondary bypass line $1_k$, $1_{k+1}$, $1_{k+2}$ provided with a valve which is typically of small diameter: $v_{i+1}$, $v_{i+3}$, $v_{i+5}$.

Each plate is also connected to a secondary bypass line $M_k$ or $M_{k+1}$ or $M_{k+2}$ provided with a relatively small diameter valve $V_{Mk}$ or $V_{Mk+1}$ or $V_{Mk+2}$.

In total, for each sector of 2 plates, there are 4 relatively large diameter network valves, 2 plate valves also with a relatively large diameter to allow the circulation of F, D, R, E etc at their nominal flow rate and two relatively small diameter bypass valves (auxiliary and secondary), namely 8 valves, giving an average of 4 valves per plate, including 3 large diameter valves. Thus, one large diameter valve per plate is gained when this device is compared with prior art FIG. 1.

The device operates as follows:

For the sector Sk, for example, when in a given period, one of the fluids F, D, R, E is to be supplied to or withdrawn from the plate $P_i$, the corresponding network valve $V_{Fk}$, $V_{Dk}$, $V_{Rk}$, $V_{Ek}$ is opened as well as the plate valve $V_i$. The other network valves of the sector Sk are then closed, as well as $V_{i+1}$ and the small secondary bypass valve $V_{Mk}$ of the upper secondary bypass line $M_k$ and the small auxiliary bypass valve $v_{i+1}$. In contrast, the small secondary bypass valve $V_{Mk+1}$ of the secondary bypass line $M_{k+1}$ is preferably open.

When in another period one of fluids F, D, R, E are to be supplied to or withdrawn from plate $P_{i+1}$, the corresponding network valve $V_{Fk}$, $V_{Dk}$, $V_{Rk}$ or $V_{Ek}$ and the plate valve $V_{i+1}$ are opened. The other network valves of $S_k$ are then closed, as well as $V_i$. The small auxiliary bypass valve $v_{i+1}$ may remain closed. The small secondary bypass valve $V_{Mk}$ of the upper secondary bypass line $M_k$ is preferably open and the small secondary bypass valve $V_{Mk+1}$ of the secondary bypass line $M_{k+1}$ is necessarily closed.

When in a third period one of fluids F, D, R, E is not to be supplied to or withdrawn from plates $P_i$ and $P_{i+1}$, the network valves $V_{Fk}$, $V_{Dk}$, $V_{Rk}$ and $V_{Ek}$ are closed. Next, a limited bypass flow is circulated in the line $L_k$ (withdrawn from $P_i$ and injected into $P_{i+1}$) by opening $V_i$, closing $V_{i+1}$ and opening the small auxiliary bypass valve $v_{i+1}$. Thus, a small bypass flow $V_{i+1}$ is ensured via $l_k$ is ensured which is typically a regulating valve (progressive opening) controlled by regulating the flow rate from a flow meter, not shown.

When in a fourth period, 1) one of fluids F, D, R, E is neither to be supplied to nor withdrawn from plates $P_i$ and $P_{i+1}$, network valves $V_{Fk}$, $V_{Dk}$, $V_{Rk}$, $V_{Ek}$ are closed, and 2) to have a zero bypass flow is required in the line $L_k$, $V_i$, $V_{i+1}$ and the small auxiliary bypass valve $v_{i+1}$ are closed. A limited bypass flow is then circulated at a limited flow rate in the secondary bypass line $M_k$ and optionally in $M_{k+1}$ except when the plates $P_{i-1}$ or $P_{i+2}$ are in the supply or withdrawal phase, in which case the corresponding secondary bypass line must remain out of service.

The other sectors $S_{k+1}$, $S_{k+2}$ function in an analogous manner.

One example of a type of function of a sector Sk is as follows, in which the valves for the function of $S_k$ which are open are mentioned and the valves which are not mentioned are closed. Only the movements in the secondary bypass in $M_k$ for flushing $P_i$ are described (not those in $M_{k+1}$)

Period 1: bypass flush from $P_i$ to $P_{i+1}$. Open valves: $V_i$, $v_{i+1}$;
Period 2: injection of desorbant into $P_i$. Open valves: $V_i$, $V_{Dk}$;
Period 3: injection of desorbant into $P_{i+1}$. Open valves: $V_{i+1}$, $V_{Dk}$, and bypass flush from $P_{i-1}$ to $P_i$. Open valve: $V_{Mk}$;
Period 4: bypass flush from $P_i$ to $P_{i+1}$. Open valves: $V_i$, $v_{i+1}$;
Period 5: withdrawal of raffinate from $P_i$. Open valves: $V_i$, $V_{Rk}$;
Period 6: withdrawal of raffinate from $P_{i+1}$. Open valves: $V_{i+1}$, $V_{Rk}$. And bypass flush from $P_{i-1}$ to $P_i$. Open valve: $V_{Mk}$;
Period 7: bypass flush from $P_i$ to $P_{i+1}$. Open valves: $V_i$, $v_{i+1}$;
Period 8: bypass flush from $P_{i-1}$ to $P_i$. Open valve: $V_{Mk}$;
Period 9: bypass flush from $P_i$ to $P_{i+1}$. Open valves: Vi, $v_{i+1}$;
Period 10: bypass flush from $P_{i-1}$ to $P_i$. Open valve: $V_{Mk}$;
Period 11: bypass flush from $P_i$ to $P_{i+1}$. Open valves: $V_i$, $v_{i+1}$;
Period 12: injection of feed into $P_i$. Open valves: $V_i$, $V_{Fk}$;
Period 13: injection of feed into $P_{i+1}$. Open valves: $V_{i+1}$, $V_{Fk}$. And bypass flush from $P_{i-1}$ to $P_i$. Open valve: $V_{Mk}$;
Period 14: bypass flush from $P_i$ to $P_{i+1}$. Open valves: $V_i$, $v_{i+1}$;
Period 15: bypass flush from $P_{i-1}$ to $P_i$. Open valves: $V_{Mk}$;
Period 16: bypass flush from $P_i$ to $P_{i+1}$. Open valves: $V_i$, $v_{i+1}$;
Period 17: bypass flush from $P_{i-1}$ to $P_i$. Open valves: $V_{Mk}$;
Period 18: bypass flush from $P_i$ to $P_{i+1}$. Open valves: $V_i$, $v_{i+1}$;
Period 19: bypass flush from $P_{i-1}$ to $P_i$. Open valves: $V_{Mk}$;
Period 20: bypass flush from $P_i$ to $P_{i+1}$. Open valves: $V_i$, $v_{i+1}$;
Period 21: withdrawal of extract from $P_i$. Open valves: $V_i$, $VL_k$;
Period 22: withdrawal of extract from $P_{i+1}$. Open valves: $V_{i+1}$, $V_{?k}$. And bypass flush from $P_{i+1}$, to $P_i$. Open valve: $V_{Mk}$;
Period 23: bypass flush from $P_i$ to $P_{i+1}$. Open valves: $V_i$, $v_{i+1}$;
Period 24: bypass flush from $P_{i-1}$ to $P_i$. Open valves: $V_{Mk}$.

The principles which allow the preferred sequencing are as follows:

1) each time one of the principal fluids (F, D, R, E) is withdrawn or injected using a network valve in a bypass line Lk, this network valve remains open two times in succession (during the successive 2 periods). The first time, the upper, open plate valve allows connection to the upper plate $P_i$, and the lower plate valve $V_{i+1}$ as well as the small valve $v_{i+1}$ controlling the auxiliary bypass fluid of line lk are closed. The second time, the lower plate valve $V_{i+1}$ is open, allows connection to the lower plate $P_{i+1}$, and the upper plate valve $V_i$ and the small fluid bypass control valve $v_{i+1}$ are closed. Further, the small control valve $V_{Mk}$ of the upper secondary bypass line $M_k$ is open to place in communication the plates $P_{i-1}$ (not shown) of sector $S_{k-1}$ (not shown) and the plate $P_i$ of the sector $S_k$.

2) Outside the periods for injection or withdrawal of the principal fluids (F, D, R, E), a bypass flow is alternately circulated in $L_k$ every other time. The upper plate valve $V_i$ is then open, the lower valve $V_{i+1}$ is closed and the small control valve $v_{i+1}$ on the auxiliary bypass around $V_{i+1}$ regulates the bypass flow via the auxiliary bypass $l_k$. Alternatively, a bypass flow circulates in the upper secondary bypass line $M_k$ regulated by the small control valve $V_{Mk}$, the two plate valves $V_{i-1}$ and $V_i$ being closed to produce a bypass between $P_{i-1}$ and $P_i$. This latter bypass flow would not, however, be brought into service if the plate $P_{i-1}$ were supplied to or withdrawn via F, D, R, E etc.

FIG. 3 shows a portion of a column of a SMB in another embodiment of the invention. The plate valves (not numbered) does not include the small auxiliary bypass line $l_k$ to limit the bypass flush flow in $L_k$, as in the device of FIG. 2. This function is ensured by a valve which typically has a progressive opening: $9_A$ for $L_k$ and $9_b$ for $L_{k+1}$. This does not allow the auxiliary lines $l_k$, $l_{k+1}$ to be used, but requires relatively large diameter valves $9_A$, $9_B$ so as not to limit the flow circulating in $L_k$.

Alternatively, a plate valve of $L_k$ may be used as a flow regulating valve instead of the valve $9_A$ and/or the valve $9_B$. This valve or these valves must thus have an enhanced seal.

Best Implementation

The best implementation of the invention is a SMB wherein the column or columns are essentially constituted by sectors $S_k$ with small valves $v_{i+1}$ etc in the auxiliary bypass of plates $P_{i+1}$ etc as seen in FIG. 2.

In such a device, there are 3 large diameter valves per plate (6 per sector $S_k$: $V_{Fk}$, $V_{Dk}$, $V_{Rk}$, $V_{Ek}$, $V_i$, $V_{i+1}$) as opposed to 4 in the prior art (see FIG. 1). On average there is one small regulating valve per plate ($V_{Mk}$ or $v_{i+1}$ for the 2 plates of $S_k$) as opposed to 0.5 in the prior art, but this valve is much cheaper and the total number of valves is reduced (4 as opposed to 4.5).

The device of the invention described above may be used for any process for chromatographic separation, in particular to separate an aromatic hydrocarbon from a feed of aromatics essentially containing 8 carbon atoms and including that hydrocarbon.

In particular, it may be used to separate para-xylene from an aromatic cut essentially composed of C8 hydrocarbons, using toluene or para-diethylbenzene as a desorbant and a zeolite as an adsorbant as described, for example, in FR-A-2 789 914. It may also be used to separate meta-xylene from an aromatic C8 cut, using toluene or tetraline as a desorbant and an adsorbant such as that described in U.S. Pat. No. 5,900,523 and patent applications FR-A-05/52.485 and FR-A-05/52.486.

It may also be used to separate one or more normal paraffins (separated from the remainder of the hydrocarbons) from a mixture of hydrocarbons, in particular paraffinic or paraffinic and naphthenic, for example using normal butane or normal pentane as the desorbant (optionally isooctane as in inert diluent) and a 5A zeolite as the adsorbant.

Finally, it may be used to separate at least one olefin from a hydrocarbon cut comprising said hydrocarbon, under conditions known in the art, for example using an X zeolite exchanged with calcium.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 06/09.192, filed Oct. 16, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A device which can separate at least one compound from a mixture comprising said compound by simulated moving bed adsorption, comprising:

at least one column comprising a plurality of adsorbant beds $A_i$ separated by distributor/extractor plates $P_i$ for sequential supply and extraction of at least two supply fluids: a feed F and a desorbant D, and at least two withdrawal fluids: a raffinate R and an extract E, $P_i$ being disposed between the bed $A_i$ and the immediately lower bed $A_{i+1}$;

the device also comprising at least one feed network F-Net, a desorbant network D-Net, a raffinate network R-Net and an extract network E-Net, each of said networks being connected to the column via a plurality of lines comprising controlled two-way isolating valves with an opening diameter of $\alpha$ or above, termed network valves, for sequential supply or withdrawal of said supply or withdrawal fluids;

in which the column is divided, over at least the major part of its height, into a plurality of adjacent superimposed sections $S_k$, each sector $S_k$ being essentially constituted by 2 successive adsorbant beds $A_i$, $A_{i+1}$ and by the 2 distributor/extractor plates $P_i$, $P_{i+1}$ which are respectively disposed immediately below $A_i$ and $A_{i+1}$;

each of the distributor/extractor plates $P_i$, $P_{i+1}$ of each of the sectors $S_k$ has a single common network for sequential supply and withdrawal of F, D, R, E;

plates $P_i$, $P_{i+1}$ of each sector $S_k$ are connected together via an external principal bypass line $L_k$ connected to each of plates $P_i$, $P_{i+1}$ of $S_k$ via a connector comprising a single two-way controlled isolating valve which belongs to said plate $P_i$ or $P_{i+1}$, termed a plate valve $V_i$ or $V_{i+1}$, with an opening diameter which is greater than or equal to the value $\alpha$ for sequential supply or withdrawal of said supply or withdrawal fluids in or from $P_i$;

each of said bypass lines $L_k$ comprises at least one controlled means for limiting the flow moving in $L_k$, which is either installed on the line $L_k$ or bypasses a plate valve $V_i$ or $V_{i+1}$ of a plate of $S_k$;

in which the bypass line $L_k$ of each of the sectors $S_k$ is connected to each of the networks F-Net, D-Net, R-Net, E-Net via a single line with an internal diameter of $\alpha$ or more comprising a single network valve, respectively $V_{Fk}$, $V_{Dk}$, $V_{Rk}$, $V_{Ek}$, which has an opening diameter of $\alpha$ or more, for sequential supply or withdrawal of fluid corresponding to F, D, R or E to or from the sector $S_k$ under consideration;

the device also comprising a plurality of external secondary bypass lines $M_k$, each of lines $M_k$ connecting the 2 adjacent sectors $S_{k-1}$ and $S_k$ via 2 connecting points;

the first connecting point being disposed on the connector connecting the lower plate $P_{i+1}$ of the upper sector $S_{k-1}$ between $P_{i+1}$ and the plate valve $V_{i-1}$;

the second connecting point being disposed on the connector connecting the upper plate $P_i$ of the lower sector $S_k$ between $P_i$ and the plate valve $V_i$;

each of the external secondary bypass lines $M_k$ comprising a controlled two-way valve $V_{Mk}$ with an internal opening diameter of $\beta$ or less, in which $\beta \leq 0.6\alpha$.

2. A device according to claim 1, in which 30 mm $1.7\times \beta \leq \alpha \leq 600$ mm.

3. A device according to claim 2, in which each of said principal bypass lines $L_k$ comprises at least one controlled means for limiting the flow circulating in $L_k$, which is installed in the auxiliary bypass around a plate valve $V_i$ or $V_{i+1}$ of a plate of $S_k$.

4. A device according to claim 1, in which the bypass line $L_k$ has an internal diameter equal to at least the largest opening diameter of the network valves connected to $L_k$.

5. A device according to claim 4, in which each of said principal bypass lines $L_k$ comprises at least one controlled means for limiting the flow circulating in $L_k$, which is installed in the auxiliary bypass around a plate valve $V_i$ or $V_{i+1}$ of a plate of $S_k$.

6. A device according to claim 1, in which the whole column with the exception of the head plate is constituted by said adjacent superimposed sections $S_k$, the column comprising a lower outlet line assimilated with a plate Pn corresponding to the lower adsorbant bed An.

7. A device according to claim 6, in which each of said principal bypass lines $L_k$ comprises at least one controlled means for limiting the flow circulating in $L_k$, which is installed in the auxiliary bypass around a plate valve $V_i$ or $V_{i+1}$ of a plate of $S_k$.

8. A device according to claim 1, in which each of said principal bypass lines $L_k$ comprises at least one controlled means for limiting the flow circulating in $L_k$, which is installed in the auxiliary bypass around a plate valve $V_i$ or $V_{i+1}$ of a plate of $S_k$.

9. A device according to claim 8, in which said means for limiting the flow circulating in $L_k$ installed in the auxiliary bypass around said plate valve $V_i$ or $V_{i+1}$ comprises a controlled valve with an opening diameter of $\beta$ or less.

10. A device according to claim 1, in which each of said secondary bypass lines $M_k$ comprises at least one controlled means for limiting the flow circulating in $M_k$, said means comprising said valve $V_{Mk}$.

11. A device according to claim 10, in which each of said principal bypass lines $L_k$ comprises at least one controlled means for limiting the flow circulating in $L_k$, which is installed in the auxiliary bypass around a plate valve $V_i$ or $V_{i+1}$ of a plate of $S_k$.

12. A device according to claim 1, comprising a sequential supply network RE-Net for a reflux fluid RE principally comprising extract, said network being connected to each of sectors $S_k$ via a single line with an internal diameter which is greater than or equal to $\alpha$, comprising a single network valve $V_{REk}$, which has an opening diameter of $\alpha$ or more.

13. A device according to claim 12, in which each of said principal bypass lines $L_k$ comprises at least one controlled means for limiting the flow circulating in $L_k$, which is installed in the auxiliary bypass around a plate valve $V_i$ or $V_{i+1}$ of a plate of $S_k$.

14. A device according to claim 1, comprising a sequential withdrawal network R2-Net for a second raffinate R2, said network being connected to each of the sectors $S_k$ via a single line with an internal diameter which is equal to or greater than $\alpha$, comprising a single network valve $V_{R2k}$ which has a diameter of $\alpha$ or more.

15. A device according to claim 14, in which each of said principal bypass lines $L_k$ comprises at least one controlled means for limiting the flow circulating in $L_k$, which is installed in the auxiliary bypass around a plate valve $V_i$ or $V_{i+1}$ of a plate of $S_k$.

* * * * *

UNITED STATES PATENT AND TRADEMARK OFFICE
CERTIFICATE OF CORRECTION

PATENT NO. : 7,582,207 B2
APPLICATION NO. : 11/907625
DATED : September 1, 2009
INVENTOR(S) : Hotier et al.

It is certified that error appears in the above-identified patent and that said Letters Patent is hereby corrected as shown below:

On the Title, Item (57), line 11 reads "line $L_k$ connected to each plate $P_1$ of $S_k$ via a large diameter", should read -- line $L_k$ connected to each plate $P_i$ of $S_k$ via a large diameter --.

On the Title, Item (57), line 12 reads "plate valve $V_1$ and an external secondary bypass line $M_k$", should read -- plate valve $V_i$ and an external secondary bypass line $M_k$ --.

Column 14, line 38, reads "A device according to claim 1, in which 30 mm 1.7x", should read -- A device according to claim 1, in which 30 mm ≤ 1.7x --.

Signed and Sealed this

Twentieth Day of October, 2009

David J. Kappos
*Director of the United States Patent and Trademark Office*